United States Patent [19]

Mandai et al.

[11] Patent Number: 5,342,441
[45] Date of Patent: Aug. 30, 1994

[54] BIOLOGICALLY COMPATIBLE HARDENING MATERIAL FOR DENTAL OR MEDICAL APPLICATIONS

[75] Inventors: Yoshinobu Mandai; Kohji Nagatomi; Kazuhiko Minamigawa; Fumihito Sugihara, all of Yao, Japan

[73] Assignee: Nitta Gelatin Inc., Osaka, Japan

[21] Appl. No.: 902,024

[22] Filed: Jun. 22, 1992

[30] Foreign Application Priority Data

Jun. 26, 1991 [JP] Japan .................................. 3-154940

[51] Int. Cl.$^5$ .............................................. A61K 6/02
[52] U.S. Cl. ................................... 106/35; 433/228.1; 423/308
[58] Field of Search ................. 106/35; 433/228.1; 423/308

[56] References Cited

U.S. PATENT DOCUMENTS

| | | |
|---|---|---|
| 4,518,430 | 5/1985 | Brown et al. . |
| 4,518,721 | 5/1985 | Dhabhar et al. ..................... 523/120 |
| 4,902,649 | 2/1990 | Kimura et al. ...................... 501/1 |
| 5,149,368 | 9/1992 | Liu et al. . |
| 5,180,426 | 1/1993 | Sumita .................................. 106/35 |

FOREIGN PATENT DOCUMENTS

| | | |
|---|---|---|
| 0389629 | 10/1990 | European Pat. Off. . |
| 3730298 A1 | 3/1988 | Fed. Rep. of Germany . |
| 59-88351 | 5/1984 | Japan . |
| 60-92202 | 5/1985 | Japan . |
| 60-253454 | 12/1985 | Japan . |
| WO90/00892 | 2/1990 | PCT Int'l Appl. . |
| WO90/01341 | 2/1990 | PCT Int'l Appl. . |

*Primary Examiner*—Paul Lieberman
*Assistant Examiner*—Margaret Einsmann
*Attorney, Agent, or Firm*—Armstrong, Westerman, Hattori, McLeland & Naughton

[57] ABSTRACT

A hardenable, biocompatible composition for repairing firm living tissue which includes a powder component containing $Ca_4P_2O_9$ and at least one of $CaHPO_4$ and $CaHPO_4 \cdot H_2O$ at a molar ratio of Ca:P of 1.16–1.95; and a liquid component containing 1 mM to 2M of a second phosphate ion and 1 mM to 2M of an organic ion. The weight ratio of the powder component to the liquid component is 0.5–4.0.

9 Claims, 8 Drawing Sheets

BIOLOGICALLY COMPATIBLE HARDENING MATERIAL FOR DENTAL OR MEDICAL APPLICATIONS

BACKGROUND OF THE INVENTION

The present invention relates to hardening materials or repairing living hard tissue which are applied to medical cements used for adhesion or mixing for repairing bone defects or gaps, dental pulp capping cements, dental root canal sealing cements, etc.

For medical cements used for adhesion and fixing for repairing bone defects and gaps in the orthopaedic surgery field, cyanoacrylate type adhesives and methyl methacrylate polymer-methyl methacrylate monomer type bone cements have been currently employed. These polymers however, are not able to integrate into hard tissue even after being retained in living body for long periods of time because their low biocompatibility. On the other hand, for root canal restoration in odontotherapy, the typical methods are of filling calcium hydroxide type pastes into root canal or of sealing root apex with zinc oxide eugenol cements together with gutta-percha points. However, there is a problem that the calcium hydroxide type pastes cause irritation because the pH of the neighborhood of the filled volume becomes too basic. Also, it has been pointed out in various fields that the zinc oxide eugenol cements show high cytotoxicity.

Recently, the granules and the block and porous forms of a calcium phosphate, hydroxyapatite [$Ca_{10}(PO_4)_6(OH)_2$; it may be called apatite hydroxide or HAP], have been clinically used as materials for repairing bone defects and gaps because of its high biocompatibility, on which many reports have been published.

These materials of hydroxyapatite, however, easily leak out from the incised part when filled into bone defects or gaps, because, although hydroxyapatite nontoxic to living body, it cannot integrate into hard tissue even after being retained in living body for long periods of time. In addition, since hydroxyapatite prepared either by dry method or by wet method does not cause a hardening reaction, it cannot be used as a substitute for the powder component of the above described cements.

Cement type materials, that is hardening materials, have exceedingly large possibility in applications of the materials because of their hardenability, adhesivity, moldability adaptable to complicated shapes and so on, unlike general ceramics (sintered substances).

Because of these reasons, hardening materials using biologically active calcium phosphates have been investigated. Thus, coagulation-hardening type materials, in which the phosphates harden by hydration reaction, and chelation-hardening type materials, in which the phosphates form chelate bonds with organic acids or carboxyl group-containing polymers contained in large amounts in the liquid component, resulting in hardening, have been proposed.

The coagulation-hardening type materials do not require of organic acids for hardening, because tile materials harden by the phenomena that the calcium phosphates cause hydration in water to coagulate and finally convert into hydroxyapatite or octacalcium phosphate [$Ca_8H_2(PO_4)_6 \cdot 5H_2O$; it may be called OCP]. Because of this reason, the coagulation-hardening type materials do not cause a lowering of pH due to the organic acids.

The biologically active calcium phosphates gradually convert into hydroxyapatite, which is a major component of living hard tissue, for example, in living body or oral cavity and Call integrate into living hard tissue. Alpha-tricalcium phosphate [$Ca_3(PO_4)_2$ (alpha-type); it may be called alpha-TCP], tetracalcium phosphate [$Ca_4(PO_4)_2O$; it may be called TeCP or 4CP], and so on are exemplified as the phosphates. Various kinds of water-hardening calcium phosphate compositions using these calcium phosphates have been proposed.

For the coagulation-hardening type material using tetracalcium phosphate, a coagulation-hardening type dental restorative paste comprising a mixture of tetracalcium phosphate and calcium hydrogen phosphate is proposed. (U.S. Pat. No. 4,518,430).

The conventional coagulation-hardening type materials have problems that they show poor kneading-processability and cannot be filled uniformly because their pastes (paste may be called cement mud or kneaded product) do not spread uniformly. In general, hardening materials are used by suitably changing the ratio of their powder to liquid components in order to control setting time. If the amount of the powder component were increased in order to shorten the setting time, the kneading-processability and filling properties of the coagulation-hardening type materials would become further poor.

Because of the reason, the hardening materials which show desired effect only when the powder and liquid components are kneaded in a range of extremely limited ratio are not useful practically.

It was found by the inventors' research that since the pH of the neighborhood of the filled pastes of the conventional coagulation-hardening type materials are acidic or highly basic regions during hardening, the materials irritated the living body.

SUMMARY OF THE INVENTION

The subject of the present invention is to provide hardening materials for repairing living hard tissue which show excellent kneading-processability and filling property of their pastes, have controllable setting time, have a weakly basic pH in the neighborhood of the filled part immediately after filling into living body, and are capable of integrating into living hard tissue.

To meet these objects, the present invention provides a hardening material for repairing living hard tissue which is made by combining a powder component containing at least tetracalcium phosphate and calcium hydrogen phosphate with a liquid component containing secondary phosphate and organic acid ions.

Tetracalcium phosphate powder used in the present invention is the calcium phosphate shown by the chemical formula $Ca_4P_2O_9$. There is no special restriction in its production method, and those prepared by any type of the production methods may be used. For example, $CaCO_3$, $CaO$, $Ca(OH)_2$, etc. as Ca sources, $P_2O_5$, $H_3PO_4$, $NH_4H_2PO_4$, $(NH_4)_2HPO_4$, etc. as P sources, and $CaHPO_4 \cdot 2H_2O$, $CaHPO_4$, $Ca(H_2PO_4)_2$, $Ca_2P_2O_7$, etc. as the both sources may be used as materials. Various preparations using combinations these materials in a Ca to P molar ratio of 2 are proposed. The dry preparation process is preferred which $Ca_2P_2O_7$ prepared by sintering $CaHPO_4 \cdot 2H_2O$ is mixed with $CaO$ prepared by sintering $CaCO_3$ in a molar ratio of 1:2 followed by sintering. The tetracalcium phosphate powder prepared by the dry method is preferred for the powder material of cements.

For calcium hydrogen phosphate used in the present invention, both its dihydrate ($CaHPO_4 \cdot 2H_2O$; it may be called DCPD and its mineral name is bragite) and anhydrous ($CaHPO_4$; it may be called DCPA and its mineral name is monetite) may be employed. Though calcium hydrogen phosphate also has no special restriction in its production method, the grade in the Japanese Pharmacopoeia is preferred.

In the present invention, not only two of tetracalcium phosphate and calcium hydrogen phosphate but also mixtures of three kinds or more of tetracalcium phosphate, calcium hydrogen phosphate, and the other calcium phosphate(s) may be used as the powder component. For example, hydroxyapatite, apatite carbonate, alpha-, alpha'-, beta-, and gamma-tricalcium phosphates, octacalcium phosphate, and the like are given as the other calcium phosphates.

The ratio of tetracalcium phosphate to calcium hydrogen phosphate is preferably in a range of 1.16 to 1.95 in the molar ratio of Ca to P (Ca/P ratio) in their mixtures, more preferably 1.28 to 1.91. Out of this range the cement may have too long of a setting time.

The ratio of the total weight of tetracalcium phosphate and calcium hydrogen phosphate to the other calcium phosphate described above is preferably 0.5 or more in the molar ratio of the total weight to the other calcium phosphate, more preferably 1 or more. Out of this range the cement also may have too long of a setting time.

In the present invention, although there is no special restriction in the particle size of the powder component, in order to make the kneading-processability of the hardening materials as easy as possible and to make the setting rate of the hardening materials as rapid as possible, the mean particle size is preferably 50 μm or less, more preferably in a range of 0.1 to 20 μm.

The liquid component used for kneading the above powder component is an aqueous solution containing secondary phosphate and organic acid ions. One or more secondary ion sources are selected from water-soluble secondary phosphates such as disodium, dipotassium, and diammonium hydrogen phosphates. One or more selected from organic acids and carboxyl group-containing polymers such as citric acid, malic acid, malonic acid, maleic acid, fumaric acid, fumaleic acid, lactic acid, acetic acid, oxalacetic acid, isocitric acid, aconitic acid, succinic acid, acrylic acid homopolymer, acrylic acid-itaconic acid copolymer, etc., and their salts may be used. The organic acids produced in the citric acid cycle of the metabolic cycle in vivo or their salts are preferred.

The concentration of the secondary phosphate ion in the liquid component is preferably 1 mM to 2M as secondary phosphate, more preferably 20 to 500 mM, and that of the organic acid ion in the liquid component is preferably 1 mM to 2M as the organic acid or as the total of organic acid and its salt, more preferably 1 to 500 mM. Concentrations of lower or higher than these ranges may cause too slow or too rapid a setting rate of the resulting cement, respectively.

The secondary phosphate and organic acid and/or its salt are used preferably in a mixture ratio of (molar concentration of secondary Phosphate)/(total molar concentration of organic acid and/or its salt) of 0.02 to 142, more preferably 0.04 to 71. A molar ration out of this range may have no capacity to buffer the liquid component. If the molar ratio were lower than the above range, it would be impossible to maintain the pH of the neighborhood of the paste in weakly basic regions, and the higher molar ratio may cause poor kneading-processability.

The forementioned liquid component is, for example, a buffer solution containing at least one kind of disodium hydrogen phosphate and dipotassium hydrogen phosphate and containing at least one kind of citric acid and malic acid.

In the hardening materials in the present invention, for example, the above powder and liquid components are kneaded preferably in a (powder weight)/(liquid weight) ratio of 0.5 to 4, more preferably 1 to 2.4. If the powder were more than this range, it would be impossible to knead the whole quantity of the powder with the liquid, and too high a liquid may cause too much flowability of the paste and inability in molding and hardening.

The hardening materials in the present invention may optionally contain a thickener to improve moldability and uniformity in filling of their pastes. As to the thickener, for example, one or more selected from water-soluble polymers such as carboxymethyl cellulose, sodium carboxymethyl cellulose, hydroxypropyl cellulose, polyvinyl alcohol, polyglutamic acid and its salts, and polyaspartic acid and its salts, etc. are proposed. At least one selected from carboxymethyl cellulose sodium, hydroxypropyl cellulose, polyglutamic acid, and polyglutamic acid salts is preferred because of their high solubility in water and moderate viscosity. The thickener may be mixed with the powder or liquid component or the paste during kneading. The preferred ratio in use depends on the type of thickener used. For example, polyglutamic acid and its salts are used preferably at 0.5 to 15% by weight to the total weight of the liquid component, more preferably at 1 to 10% by weight, and the other thickeners are used preferably at 0.5 to 10% by weight, more preferably at 0.5 to 5% by weight.

The hardening materials in the present invention may optionally contain a X-ray contrast medium. The use of the medium is capable of monitoring upon filling the pastes the hardening materials and searching the change after filling. One or plural kinds selected from barium sulfate, bismuth(III) carbonate (bismuth oxycarbonate), iodoform, barium apatite, barium titanate, etc. is given for the X-ray contrast medium. It may be mixed with the powder or liquid component or the paste during kneading. For example, its amount for use at 5 to 30% by weight to the total weight of the powder component is preferred.

The hardening materials in the present invention may contain starch, glucosaminoglycane, alginic acid, chitin, chitosan, heparin, etc. as polysaccharides other than cellulose, collagen, gelatin, and thief derivatives as proteins, and antirheumatic agents, antiphlogistics, antibiotics, anti-cancer agents, bone-inducing factors, tannic acid and its derivatives such as catechin, retinoic acid and its derivatives. Depentaplegic-Vg-related family (which may be called DVR gene family), TGF-$\beta$1, TGF-$\beta$2, TGF-$\beta$ family, etc. in addition to the above essential and optional components.

The hardening materials in the present invention are used in the same manner as for the conventional hardening materials employed in the medical and dental fields. For example, the above essential and optional components are kneaded to form a paste. Since the paste hardens, Lot example in 5 to 30 minutes to be unable to deform the paste should be filled into defect according to the usual method before completion of hardening. The filled paste hardens under living body or oral cavity environment and converts completely into hydroxyapatite, for example, in day, and the hardened substance is partially displaced into new bone and finally integrates into living hard tissue.

The hardening materials in the present invention are used, for example, as medical cements for adhesion or fixing, dental pulp capping cements, dental root canal sealing cements and so on.

When used in the above applications, in the comparison with the conventional hardening materials, the hardening materials of the present invention are excellent in the following points; superior kneading-processability to that of the conventional hardening materials, good filling properties of their pastes, controllable setting time region longer than few mixtures, stable pH of the neighborhood of their pastes in a weakly basic region from the initial stage, conversion of their pastes into hydroxyapatite in living body or oral cavity in short periods of time, promotion of forming living hard tissue such as new bone in the neighborhood of the volume and finally integrating into living hard tissue to such an extent that the face (interface) where the paste comes in contact with the hard tissue cannot be perceived because the paste surface is replaced by the new bone.

The hardening materials in the present invention convert into hydroxyapatite in short periods of time, because the powder component contains at least tetracalcium phosphate and calcium hydrogen phosphate.

Because the liquid component contains secondary phosphate and organic acid ions, the setting time of the materials is reduced and the pH lies in a weakly basic region (for example pH 8.0 to 9.0) from the initial stage hardening of the materials axed is stabilized in the region.

The hardening materials in the present invention show excellent kneading-processability and uniform filling property of their pastes and can be adjusted at moderate setting time. In addition, the pH of the neighborhood the filled paste part immediately after filling into living body lies in a weakly basic rigion, and the materials are capable of integrating into living hard tissue.

When the hardening materials contain the thickener as well, they have an advantage of being further improved in the kneading-processability.

When the hardening materials contain the X-ray contrast medium as well, the conversion or them into living hard tissue can be monitored by radiography.

DESCRIPTION OF THE PREFERRED EMBODIMENTS

Specific examples and reference examples of the present invention are described below, but the invention is not to be limited to these examples.

Method of Measurement

1. Mean particle size

The particles obtained were dispersed in isopropyl alcohol followed by measuring the particle size by means of a particle size distribution meter (CAPA-700; made by Horiba Seisakusho), in which the principle of the method is centrifugal sedimentation.

2. Structure

The structure of tetracalcium phosphate produced and the reaction products obtained by kneading and hardening the hardening materials was identified by using a X-ray powder diffraction system (MXP$^3$; made by Max Science Co.).

3. Setting time of hardening material

The measurement is based on the method of measuring setting time of dental root canal filling materials in the International Organization for Standardization Standard. Thus, pastes obtained by kneading hardening materials for 1 minute were filled in a ring mold with a diameter of 10 mm and a height of 2 mm and, after 2 minutes from the start of kneading, measured by using a Gilmore-type needle with a mass of 100 g and a diameter 2 mm under a condition of 37° C. and a relative humidity of not less than 95%. The time until indentations cease to be visible was the setting time. The measurement was done up to 2 hours, and any time exceeding 2 hours was expressed as 'not hardening'.

4. pH of neighborhood of paste

The pH was measured by using a compact pH meter (CARDY; made by Horiba Seisakusho). Briefly, a water-absorbing paper was placed on the sensor of the pH meter, 2 or 3 drops of distilled water were dropped thereon to wet the paper, and pastes obtained by kneading hardening materials for 1 minute were placed on the wetted paper. The pH values measured at 3, 5, 10, 15, and 20 minutes after the start of kneading at room temperature were taken as the pH of the neighborhood of the pastes.

5. Kneading processability

Materials from which the pastes adhered to the kneading spatula during kneading were judged as "good kneading processability". The other judgements were based on feel to the touch.

6. Integration into living tissue

Pastes were filled into root canal of the supramandibular first molar of SD rats as direct capping agents, the rats were bred and sacrificed, and sections were prepared in accordance with the usual method. The evaluation was pathologic-histologically done with the guidance of calcification in the root canal pulp.

EXAMPLE 1 FOR PREPARATION OF POWDER COMPONENT

Calcium pyrophosphate ($Ca_2P_2O_7$) prepared by sintering calcium hydrogen phosphate dihydrate ($CaHPO_4.2H_2O$; made by Hoeiyakkou Co. Ltd.; Grade in the Japanese Pharmacopoeia) at 1,100° C. was mixed with calcium oxide prepared by sintering calcium carbonate ($CaCO_3$; made by Ebisu Yakuhin Kogyo Co. Ltd.; Grade in the Japanese Pharmacopoeia) at 1,100° C. in a molar ratio of 1:2 and then sintering at 1,400° C. The resulting product was pulverized by using a ball mill and then classified to recover particles with a particle size of not larger than 32 $\mu$m. The obtained powder was confirmed as pure tetracalcium phosphate by the identification using the X-ray powder diffraction system, in which all the peaks obtained were equal to those of the tetracalcium phosphate in the JSPD Card No. 25-1137.

The tetracalcium phosphate (mean particle size 9.2 $\mu$m) and calcium hydrogen phosphate (mean particle size 5.8 $\mu$m; the above described calcium hydrogen phosphate dihydrate) which had been classified to a particle size of not larger than 32 $\mu$m were mixed in the various molar ratios shown in Tables 2-4 to give powder components (powder material sample).

Preparation of liquid component

Aqueous solutions were prepared using the constituents at concentrations shown in Table 1 and used in the following examples and reference examples.

TABLE 1

| $Na_2HPO_4$-CITRIC ACID BUFFER SOLUTION | | | | | | |
|---|---|---|---|---|---|---|
| | | | \multicolumn{4}{c}{No.} |
| | | | I | II | III | IV |
| M/5 | $Na_2HPO_4$ | (ml) | 10.30 | 12.63 | 16.47 | 19.45 |
| M/10 | citric acid | (ml) | 9.70 | 7.37 | 3.53 | 0.55 |
| | pH | | 5.0 | 6.0 | 7.0 | 8.0 |

EXAMPLES 1-9, 12-15 and REFERENCE EXAMPLES 1-3

Hardening materials were prepared using the powder and liquid components shown in Tables 2-4 at the powder to liquid ratios (powder weight/liquid weight) shown in Tables 2-4.

REFERENCE EXAMPLE 4

A hardening material was prepared in the same manner as Example 1 except for using distilled water as the liquid component.

REFERENCE EXAMPLE 5

A hardening material was prepared in the same manner as Example 1 except for using 20 mM orthophosphoric acid as the liquid component.

REFERENCE EXAMPLE 6

A hardening material was prepared in the same manner as Example 2 except for using, as the liquid component, a glycine-NaCl-HCl buffer solution (pH 1.42) of the following composition:
0.1M glycine+0.1M NaCl; 3.0 mL
0.1 N HCl; 7.0 mL

REFERENCE EXAMPLE 7

A hardening material was prepared in the same manner as Example 2 except for using, as the liquid component, the disodium citrate-HCl buffer solution (pH 4.89) of the following composition:
0.1M disodium citrate; 9.5 mL
0.1 N HCl; 0.5 mL

REFERENCE EXAMPLE 8

A hardening material was prepared in the same manner as Example 2 except for using, as the liquid component, a glycine-NaCl-NaOH buffer solution (pH 11.25) of the following composition:
0.1M glycine+0.1M NaCl; 5.0 mL
0.1 N NaOH; 5.0 mL

EXAMPLE 10

A hardening material was prepared using the powder component prepared as the above-described method using the molar ratio shown in Table 3 and the disodium hydrogen phosphate-citric acid buffer solution (pH 5.0) containing 2.5% by weight of carboxymethyl cellulose sodium (shown as CMCNa in the Table) in a powder to liquid weight ratio of 1.4.

REFERENCE EXAMPLE 9

A hardening material was prepared in the same manner as example 10 except for use distilled water containing 2.5% by weight of carboxymethyl cellulose as the liquid component and a powder to liquid weight ratio of 1.0.

EXAMPLE 11

A hardening material was prepared in the same manner as example 10 except using a X-ray contrast medium (compound name; iodoform) at 30% by weight to the total weight of the powder component.

REFERENCE EXAMPLE 10

A hardening material was prepared using calcium oxide as the powder component and physiological saline as the liquid component.

EXAMPLES 16-30 and REFERENCE EXAMPLES 11-20

The hardening materials prepared in Examples 1-15 and Reference Examples 1-10 were kneaded to example kneading-processability, setting time, and pH of the neighborhood of the pastes in accordance with the above described methods. The results are shown in Tables 2–4.

Figure 1:
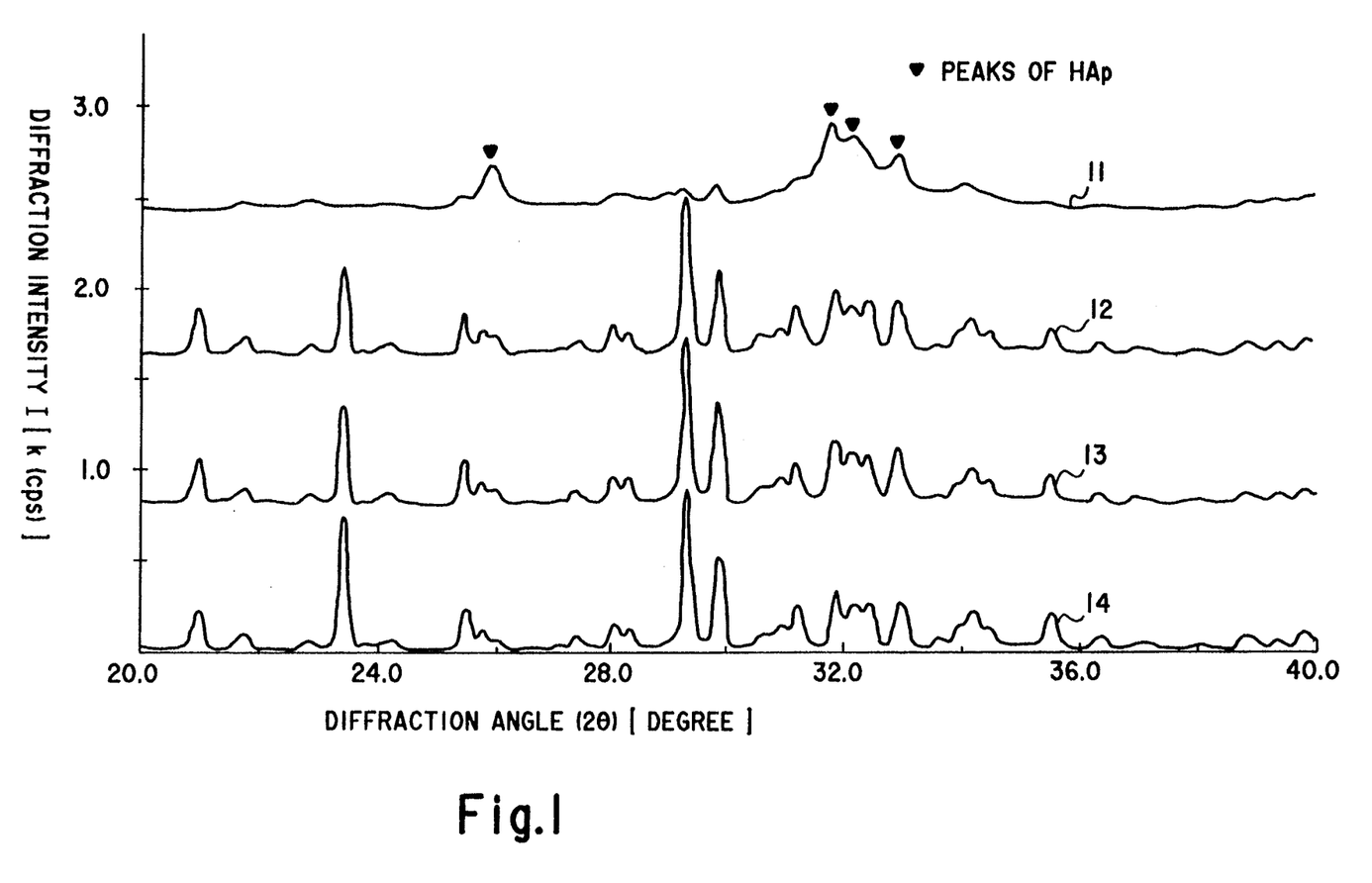
FIG. 1 shows X-ray diffraction patterns of the hardened products from the hardening materials in Example 1 and Reference Examples 4 and 5.

In the tables, 4CP, DCPD, DSP, DPP, DSC, HAp, CA, and MA represent tetracalcium phosphate, calcium hydrogen phosphate dihydrate, disodium hydrogen phosphate 12 hydrate, dipotassium hydrogen phosphate anhydrous, disodium citrate, hydroxyapatite, citric acid, and malic acid, respectively.

ucts prepared by allowing the pastes from the hardening materials in Example 1 and Reference Examples 4 and 5 to stand for 16 hours in an atmosphere of 37° C. and a relative humidity of more than 95% are shown.

Figure 2:
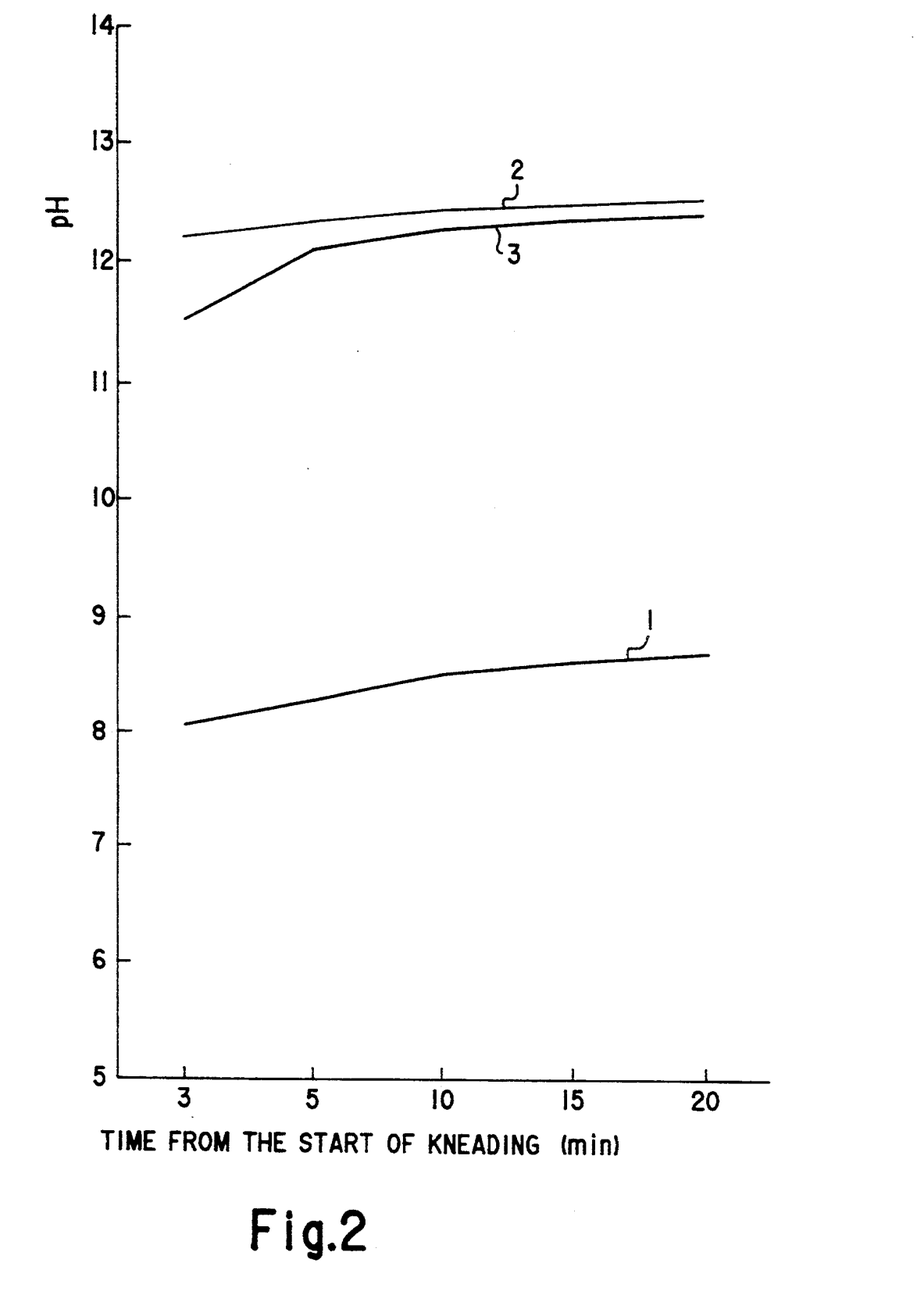
FIG. 2 shows changes in pH of the neighborhood of the pastes over time of the hardening materials in Example 1 and Reference Examples 4 and 5 from the start of kneading.

In FIG. 2, the changes in pH of the neighborhood of the pastes over time of the hardening materials in Example 1 and Reference Examples 4 and 5 from the start of kneading is shown.

TABLE 2

|  |  | EXAMPLE | | | | | | | | |
|---|---|---|---|---|---|---|---|---|---|---|
|  |  | 1 | 2 | 3 | 4 | 5 | 6 | 7 | 8 | 9 |
| Powder Component | 4CP:DCPD Molar Ratio | 1:1 | 1:1 | 1:1 | 1:1 | 1:1 | 1:3 | 3:1 | 1:5 | 5:1 |
| Liquid Component | DSP-CA Buffer Soln. (No.) | I | I | II | III | IV | I | I | I | I |
| Powder/Liquid Wt. Ratio | | 1.0 | 1.6 | 1.6 | 1.6 | 1.6 | 1.6 | 1.6 | 1.6 | 1.6 |
| Kneading-Processability | | good | good | good | good | good | good | good | good | good |
| Setting Time (min.) | | 105 | 45 | 18 | 8 | 7 | 38 | 45 | 36 | 41 |
| pH of Neighborhood of paste | After 3 min. | 8.03 | 8.61 | 8.59 | 9.08 | 8.77 | 8.57 | 7.85 | 8.76 | 7.70 |
|  | After 20 min. | 8.53 | 8.80 | 8.81 | 8.98 | 8.63 | 8.66 | 8.51 | 8.86 | 8.31 |

TABLE 3

|  |  | EXAMPLE | | | | | |
|---|---|---|---|---|---|---|---|
|  |  | 10 | 11 | 12 | 13 | 14 | 15 |
| Powder Component (Molar Ratio) | 4CP | 1 | 1 | 2 | 1 | 1 | 1 |
|  | DCPD | 1 | 1 | 2 | 1 | 1 | 1 |
|  | HAp | — | — | 1 | — | — | — |
|  | $CHI_3$ (wt. %) | — | 30 | — | — | — | — |
| Liquid Component (Wt. %) | DSP | I | I | I | 10 | — | 10 |
|  | DPP | in | in | in | — | 10 | — |
|  | CA | Tab. 1 | Tab. 1 | Tab. 1 | 5 | 5 | — |
|  | MA | — | — | — | — | — | 5 |
| Other Component |  | CMCNa | CMCNa | CMCNa | CMCNa | CMCNa | CMCNa |
| Powder/Liquid Wt. Ratio |  | 1.4 | 1.4 | 1.2 | 1.2 | 1.2 | 1.2 |
| Kneading-Processability |  | good | good | good | good | good | average |
| Setting Time (min.) |  | 42 | 53 | 46 | 9 | 10 | 14 |
| pH of Neighborhood of paste | After 3 min. | 8.40 | 8.51 | 8.26 | 7.61 | 7.81 | 7.87 |
|  | After 20 min. | 8.76 | 8.78 | 8.62 | 8.07 | 8.20 | 7.94 |

TABLE 4

|  |  | REFERENCE EXAMPLE | | | | | | | | | |
|---|---|---|---|---|---|---|---|---|---|---|---|
|  |  | 1 | 2 | 3 | 4 | 5 | 6 | 7 | 8 | 9 | 10 |
| Powder Component | 4CP:DCPD Molar Ratio | 1:0 | 1:1 | 1:1 | 1:1 | 1:1 | 1:1 | 1:1 | 1:1 | 1:1 | $Ca(OH)_2$ |
| Liquid Component |  | I in Tab. 1 | 0.2M DSP Soln. | 0.1M CA Soln. | D.W. | 20 mM $H_3PO_4$ Soln. | Gly-NaCl-HCl | DSC-HCl | Gly-NaCl-NaOH | D.W. | P.S. |
| Other Component |  | — | — | — | — | — | — | — | — | CMCNa | — |
| Powder/Liquid Wt. Ratio |  | 1.6 | 1.0 | 1.0 | 1.0 | 1.0 | 1.6 | 1.6 | 1.6 | 1.0 | 1.4 |
| Kneading Processability |  | poor | poor | poor | poor | poor | average | average | average | lump formation | average |
| Setting Time (min.) |  | n.h. | 28 | n.h. | n.h. | n.h. | 44 | 53 | 29 | — | n.h. |
| pH of Neighborhood of Paste | After 3 min. | 6.76 | 9.11 | 5.70 | 12.19 | 11.48 | 12.31 | 12.53 | 12.69 | — | 12.89 |
|  | After 20 min. | 6.76 | 8.98 | 7.01 | 12.42 | 12.30 | 12.59 | 12.78 | 12.71 | — | 12.97 |

D.W.; distilled water
Gly-NaCl-HCl; Glycine-NaCl-HCl buffer solution
DSC-HCl; disodium citrate-HCl buffer solution
Gly-NaCl-NaOH; Glycine-NaCl-NaOH buffer solution
P.S.; physiological saline
n.h.; not hardened As can be seen in Tables 2–4, the hardening materials in these examples showed good kneading-processability, the setting time was controllable at 7 minutes or more, and the pH of the neighborhood of their pastes lay in weakly basic regions at the initial stage of hardening from the start of kneading.

Figure 3:
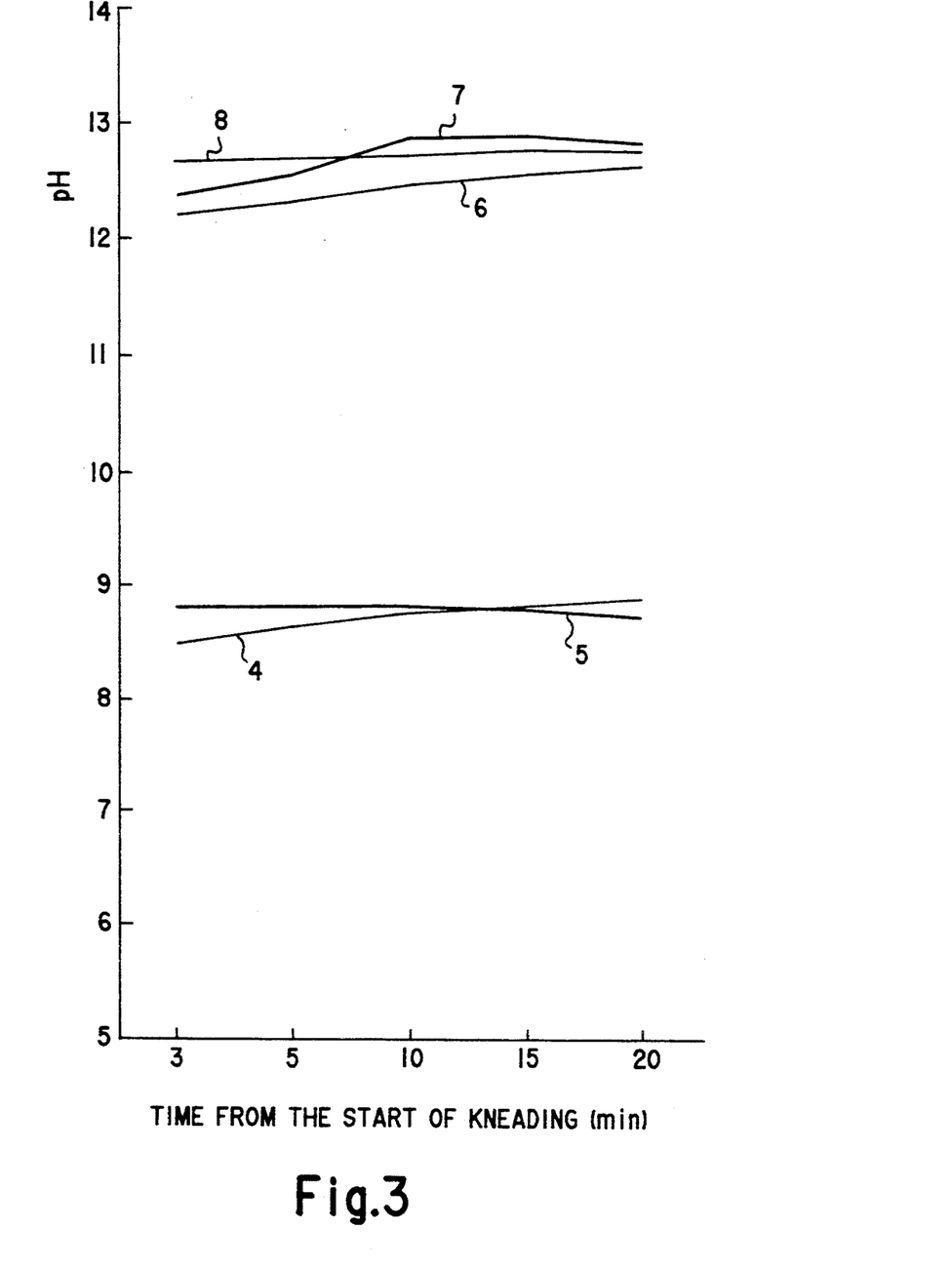
FIG. 3 shows changes in pH of the neighborhood of the pastes over time of the hardening materials in Examples 2 and 5 and Reference Examples 6–8 from the start of kneading.

In FIG. 1, the results of the identification using the X-ray powder diffraction system for the hardened prod- In FIG. 3, the pH change over time of Example 2 and 5 and Reference Examples 6–8 is shown.

As can be seen in curve 1 shown in FIG. 2, for the hardening material (Example 1), which was kneaded with the disodium hydrogen phosphate-citric acid buffer solution (pH 5.0), the pH of the neighborhood of the paste was stabilized at a weakly basic pH of about 8.5 at 20 minutes after the start of kneading. Also, for this hardening material the powder component converted into poorly crystalline hydroxyapatite at 16 hours after the start of kneading, as shown in pattern 11 in FIG. 1. In contrast, for the hardening materials using distilled water (Reference Example 4; curve 2 in FIG. 2) and 20 mM orthophosphoric acid solution (Reference Example 5; curve 3 in FIG. 2), respectively, the pH of the neighborhood of these pastes was both stabilized at a highly basic pH of about 12.5 at 20 minutes after the start of kneading. In addition no change in the morphology of these powder components was observed after 16 hours [patterns 12 (Reference Example 4) and 13 (Reference Example 5) in FIG. 1]. The pattern 14 in FIG. 1 shows the result of the powder component used in Example 1.

For the hardening materials (Examples 2-5) which were kneaded with the disodium hydrogen phosphate-citric acid buffer solution (pH 5.0-8.0), when the pH of the buffer solution is 5.0, the setting time was increased and, when the pH is 8.0, the setting time was reduced. Thus, it was shown that higher pH of the liquid tended to shorten the setting time. In addition the pH of the neighborhood of those pastes was stabilized at a weakly basic region (pH 8.0-9.0) at 20 minutes after kneading in all the pH of the solutions [curves 4 (Example 2) and 5 (Example 5) in FIG. 3]. In contrast, when using the glycine-NaCl-HCl, glycine-NaCl-NaOH, and disodium citrate-HCl buffer solutions, respectively, the pastes hardened in 1 hour, but the pH of the neighborhood of these pastes was stabilized at a highly basic region (pH 12.5-13.0) in all the buffer solutions [curves 6 (Reference Example 6), 7 (Reference Example 7) and 8 (Reference Example 8) in FIG. 3].

When distilled water containing 2.5% by weight of carboxymethyl cellulose sodium was used as the liquid component, the hardening material formed lumps during kneading and the processability was poor (Reference Example 9).

Subsequently, the integration into living hard tissue for the hardening materials in Examples 2, 10, 11, 13, and 14 and Reference Example 10 and the identification of the hardened products by X-ray powder diffraction for those in Examples 2, 10, 11, 13, and 14 and Reference Examples 4 and 5 were investigated.

The integration into living hard tissue was examined in such a manner that hardening materials (pastes) were filled into root canal of SD rats as direct capping agents and the pulp reaction was pathologic-histologically evaluated. Thus, it was examined whether or not there were lesions in the root apex and calcification occurred or not (when calcification was observed, the time when it occurred and the place in the root canal where it occurred were also examined). These results were compared with that of the hardening material using calcium hydroxide as the powder component (Reference Example 10), which has at present been used as a pulp capping agent in the dental field.

Thus, a pulp chamber of the supramandibular first molar of SD rats was opened by using a #½ found bar (a dental rotating cutting machine which is one of cutting tool for electric engine) (to make a hole in the molar so as to penetrate to the pulp cavity). The pulp cavity from which the corona dentis pulp was mechanically removed was filled with the material and sealed with a glass-ionomer cement (one of dental cements used for adhesion of metallic restorative dental materials, pulp capping, filling anterior teeth, and so on). A molar filled with a sterilzed stype and retained opened pulp cavity until completion of the experiment was used as a control. The rats were sacrificed 1, 2, 3, 4, and 5 weeks after bred, the mandibulae were taken out, demineralized, and paraffin-embedded as the usual method, and continuous sections with a thickness of approximately 5 $\mu$m were made, hematoxylin orange-dyed, and then examined pathologic-histologically.

The identification of the hardened products by X-ray powder diffraction was performed in such a manner that hardening materials were kneaded and then allowed to stand for 16 hours in an atmosphere of 37° C. and a relative humidity of not less than 95%, and the resulting hardened products were subjected to the X-ray powder diffraction system to examine whether the change of the powder components occurred or not.

It was seen that the pulp necrosed with the passage of time and the formation of apical lesions was observed after 4 weeks for the control. In contrast, for the hardening materials in Examples 2, 10, 11, 13, and 14, marked addition of hard tissue to the root canal wall was found after 3 weeks, and the whole of the root canal was sealed by hard tissue after 5 weeks. Additionally inflammation and necrosis of the pulp tissue were not seen during the experiment in these examples. For the hardening material in Reference Example 10 which comprises calcium hydroxide kneaded with physiological saline, although the material was calcified at the corona dentis side of the upper area or the root canal to form dentin bridge (a scientific name of a hard tissue having dentin-like structure) after 2-4 weeks, congestion was found at the middle area of the root canal after 3 weeks. As the results of X-ray powder diffraction, all the hardened products in these examples converted into hydroxyapatite at 16 hours after kneading. The above-described dentin bridge formed by calcium hydroxide has a structure which causes difficulty in mechanical treatment of root canal that is frequently necessary and, therefore, is not always to be a desired pulp taction. In contrast, since the whole of the root canal was sealed by hard tissue as shown above when the hardening materials for repairing living hard tissue in the present invention were used, the materials are useful as medial cements, dental pulp capping cements, dental canal sealing cements and the like for adhesion or fixing which utilize the characteristics of inducing the formation of hard tissue.

PREPARATION EXAMPLE 2

A powder component is prepared in the same manner as example 1 for the preparation of powder component except for using a 1:1 molar ratio mixture of tetracalcium phosphate having a mean particle size of 15.8 $\mu$m and calcium hydrogen phosphate dihydrate having a mean particle size of 5.9 $\mu$m and used in the following examples and reference examples. (Hereinafter, this powder component is referred to as "TeDCPD".)

EXAMPLES 31-35

Hardening materials in the present invention were prepared using the combinations of TeDCPD and the buffer solutions shown in Table 5.

TABLE 5

| No. | Constituent and pH Value | | |
|---|---|---|---|
| 1 | $Na_2HPO_4$ - citric acid type buffer solution<br>0.2M $Na_2HPO_4$ 10.30 ml + 0.1M citric acid 9.70 ml | (pH 5) | |
| 2 | 0.4M $Na_2HPO_4$ 10.30 ml + 0.2M citric acid 9.70 ml | (pH 5) | |
| 3 | $Na_2HPO_4$ - malic acid type buffer solution<br>0.2M $Na_2HPO_4$ 10.30 ml + 0.1M malic acid 9.70 ml | (pH 5.8) | |
| 4 | 0.4M $Na_2HPO_4$ 10.30 ml + 0.2M malic acid 9.70 ml | (pH 5.8) | |
| 5 | $K_2HPO_4$ - citric acid type buffer solution<br>0.4M $K_2HPO_4$ 10.30 ml + 0.2M citric acid 9.70 ml | (pH 5) | |

REFERENCE EXAMPLES 21-27

Hardening materials were prepared using the combinations of TeDCPD and the buffer solutions shown in Tables 6 and 7.

The materials in Examples 31-35 and Reference Examples 21-27 were kneaded at the powder to liquid ratios (powder weight/liquid weight) shown in Tables 6 and 7 and examined kneading-processability, setting time, and pH of the neighborhood of the pastes (at 5 and 20 minutes after the start of kneading) as above described. The results are shown in Tables 6 and 7, in which excellent in kneading-processability means occurrence of viscosity during kneading.

hour while the pH of the neighborhood of the pastes was maintained at a weakly basic region throughout after the start of kneading. The occurrence of viscosity during kneading smoothes kneading, and hence the operation of kneading becomes easy. Furthermore, since the paste having viscosity shows good spreadability, the paste can be filled uniformly and easily.

For the both of the materials in Reference Example 21 which were kneaded with distilled water, the kneading-processability was poor and the pH of the neighborhood of the pastes was in a highly basic region even on changing the powder to liquid ratio.

For the material in Reference Example 22 which was kneaded with physiological saline, the kneading-proc-

TABLE 6

| | | EXAMPLE 31 | EXAMPLE 32 | | | | EXAMPLE 33 |
|---|---|---|---|---|---|---|---|
| Liquid Component | | (1) in Tab. 5 | (2) in Tab. 5 | (2) in Tab. 5 | (2) in Tab. 5 | (2) in Tab. 5 | (3) in Tab. 5 |
| Powder/Liquid Wt. Ratio | | 1.6 | 1.0 | 1.6 | 2.0 | 2.4 | 1.6 |
| Kneading-Processability | | excellent | good | excellent | excellent | average | excellent |
| Setting Time (min.) | | 40 | 24 | 20 | 11 | 10 | 10 |
| pH of Neighbor- | After 5 min. | 8.59 | 8.49 | 8.62 | 8.43 | 8.46 | 8.47 |
| hood of Paste | After 20 min. | 8.69 | 8.60 | 8.68 | 8.56 | 8.57 | 8.56 |

| | | EXAMPLE 34 | EXAMPLE 35 | REFERENCE EXAMPLE 21 | REFERENCE EXAMPLE 22 |
|---|---|---|---|---|---|
| Liquid Component | | (4) in Tab. 5 | (5) ini Tab. 5 | distilled water | physiological saline |
| Powder/Liquid Wt. Ratio | | 1.6 | 1.6 | 1.0 | 1.6 | 1.6 |
| Kneading-Processability | | excellent | excellent | poor | poor | poor |
| Setting Time (min.) | | 7 | 14 | n.h. | 26 | 24 |
| pH of Neighbor- | After 5 min. | 8.34 | 8.51 | 12.35 | 12.50 | 12.26 |
| hood of Paste | After 20 min. | 8.39 | 8.62 | 12.48 | 12.69 | 12.40 | n.h.; not hardened

TABLE 7

| | | REFERENCE EXAMPLE | | | | |
|---|---|---|---|---|---|---|
| | | 23 | 24 | 25 | 26 | 27 |
| Liquid Component | | 20 mM $H_3PO_4$ | 0.2M DSP | 0.4M DSP | 0.1M CA | 0.2M CA |
| Powder/Liquid Wt. Ratio | | 1.0  1.6 | 1.6 | 1.6 | 1.6 | 1.6 |
| Kneading Processability | | poor  average | average | average | good | good |
| Setting Time (min.) | | n.h.  19 | 6 | 8 | n.h. | n.h. |
| pH of Neighbor- | After 5 min. | 8.31  12.29 | 9.00 | 9.23 | 5.83 | 5.41 |
| hood of Paste | After 20 min. | 8.34  12.17 | 9.04 | 8.73 | 6.33 | 5.52 | n.h.; not hardened

Figure 4:
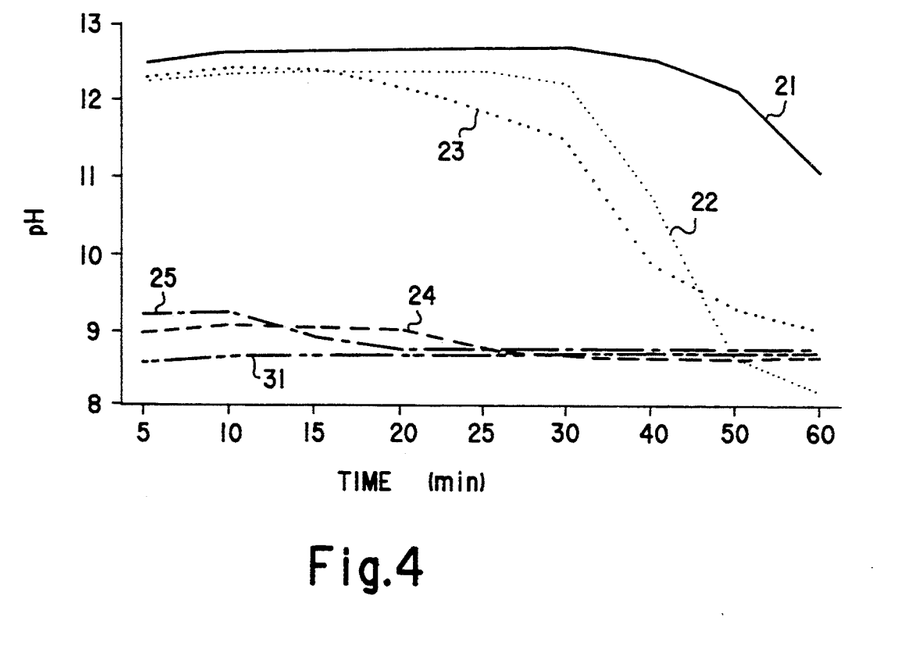
FIG. 4 shows changes in pH of the neighborhood of the pastes over time of the hardening materials using different liquid components (Example 31 and Reference Examples 21–25) from the start of kneading.

The changes in pH of the neighborhood of the pastes from the materials using a powder to liquid ratio of 1.6 in Example 31 and Reference Examples 21-25 are shown in FIG. 4. The curves 31, 21, 22, 23, 24, and 25 in FIG. 4 correspond to Example 31 and Reference Examples 21, 22, 23, 24, and 25, respectively.

The following is clear from the results shown in Tables 6 and 7 and FIG. 4;

The hardening materials in Examples 31-35 produced viscosity during kneading and hardened in less than 1 essability was poor and the pH of the neighborhood of the paste lay in a highly basic region until completion of hardening from the start the start of kneading.

The materials in Reference Example 23 which were kneaded with orthophosphoric acid at powder to liquid ratio of 1.0, did not harden and the pH of the neighborhood of the paste in a ratio of 1.6, which hardened, lay in a highly basic region until completion of hardening from the start of kneading. The material in Reference Example 23 which was kneaded in a powder to liquid ratio of 1.0 was of the same condition as reference Example 5, and hence the same result would be expected. The pH of the neighborhood of the paste, however, was largely different from each other. It is assumed that the use of the powder component having different particle size causes the different result.

When the pastes which are highly basic in the pH of the neighborhood of the pastes such as in Reference Examples 21-23, are filled into a hemorrhagic diseased part, they cause hemolysis and congestion, and hardening of them is inhibited. In addition, the pastes flow out from the diseased part with the flow of blood because they have hemostatic function.

For the materials in Reference Examples 24 and 25 which were kneaded with the disodium hydrogen phosphate solutions, the smoothness on kneading was poor and the pH in the neighborhood of the pastes was slightly more basic at the initial stage in comparison with those in Examples 31-35.

The materials in Reference Examples 26 and 27 caused neither coagulation-hardening nor chelation-hardening entirely because the concentration of the citric acid solution was low.

The materials in Examples 31 and 32 and Reference Examples 21 and 23-27 were kneaded in a powder to liquid ratio of 1.0 and examined over time (at 3, 5, 10, 15, 20, 25, 30, 40, 50, and 60 minutes after the start of kneading) for changes in the pH of the neighborhood of these pastes, The results are shown in FIGS. 5-12. In each figure, the changes in the pH of the neighborhood of: the pastes prepared by kneading each of the tetracalcium phosphate and calcium hydrogen phosphate, which were used in preparation example 2 of powder component, with the same liquid component as used for kneading TeDCPD were similarly examined and shown. In these figures, curves TeCP DCPD correspond to the pH changes on kneading the tetracalcium phosphate and calcium hydrogen phosphate, respectively.

Figure 7:
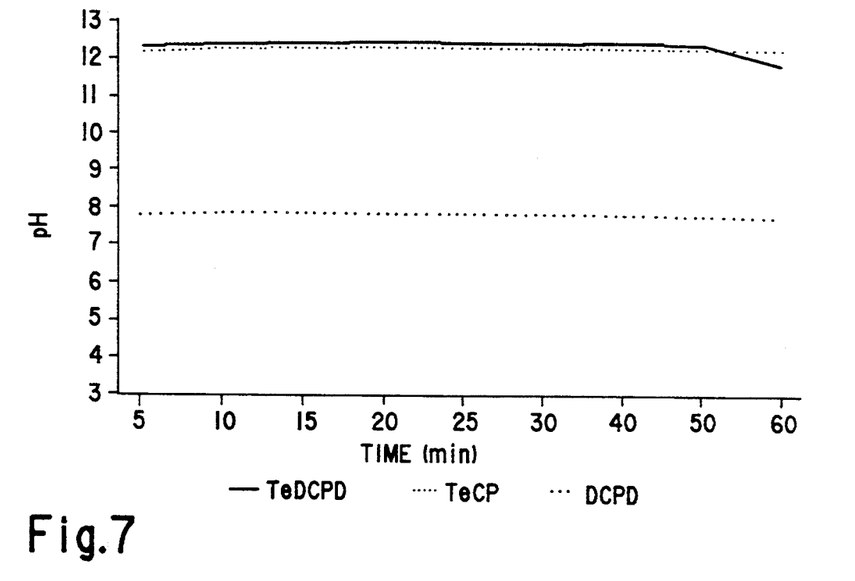
FIG. 7 shows changes in pH of the neighborhood of the pastes over time of the hardening material in Reference Example 21 and the materials using different powder components from the start of kneading.

Calcium hydrogen phosphate dissolves in distilled water and attains equilibrium as the formula 1 (see FIG. 7):

(1)

The equilibrated solution is a saturated aqueous calcium hydrogen phosphate solution and its calculated pH value is 8.8. Calcium hydrogen phosphate hydrates in the equilibrated solution as shown in the formula 2 to convert into hydroxyapatite:

(2)

Since this equilibrated solution is supersaturated with respect to hydroxyapatite, the formed hydroxyapatite deposited. When the conversion shown in the formula 2 proceeds, the pH of the solution rapidly lowers with the deposition of hydroxyapatite and attains equilibrium at the near crossing (approximately pH 4.5) of the solubility curves of calcium hydrogen phosphate and hydroxyapatite. After the solution attains equilibrium at this pH, the hydroxyapatite is not deposited. In order to continue the deposition of hydroxyapatite it is necessary to maintain the pH of the solution at a weakly basic (for example pH 7.5-10).

Tetracalcium phosphate dissolves in distilled water to attain equilibrium as shown in the formula 3 (see FIG. 7):

(3)

The equilibrated solution is a saturated aqueous solution of tetracalcium phosphate which is highly basic (pH of 12 or more), and is supersaturated with respect to hydroxyapatite.

Tetracalcium phosphate causes the following reaction as shown in the formula 4 to convert into hydroxyapatite in the equilibrated solution, and the formed hydroxyapatite is deposited:

(4)

When the reaction 4 proceeds, the pH of the solution rises because of the calcium hydroxide formation. In general, calcium phosphates are freely soluble in acidic solutions and slightly soluble in basic solutions. Therefore, since the rise of the pH of the solution result in decrease in the reaction rate, coagulation-hardening cannot be expected.

Hydroxyapatite dissolves in distilled water by the reaction as shown in the formulae 5 and 6 to attain equilibrium:

(5)

(6)

In accordance with these reactions, the calcium hydroxide formed on the conversion of tetracalcium phosphate into hydroxyapatite is also able to produce hydroxyapatite via $Ca_2(HPO_4)(OH)_2$ in the presence of secondary phosphate ion.

Figure 5:
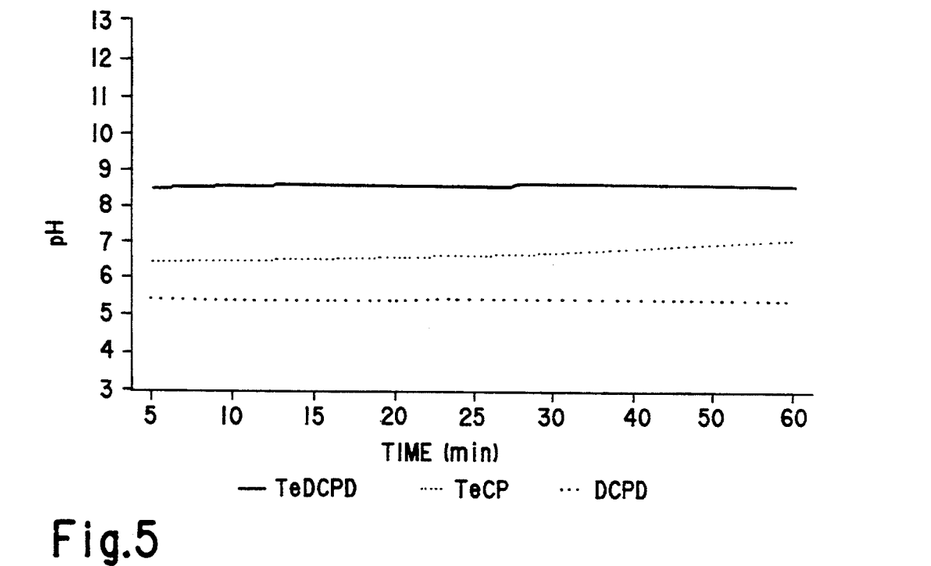
FIG. 5 shows changes in pH of the neighborhood of the pastes over time of the hardening material Example 31 and the materials using different powder components from the start of kneading.
Figure 6:
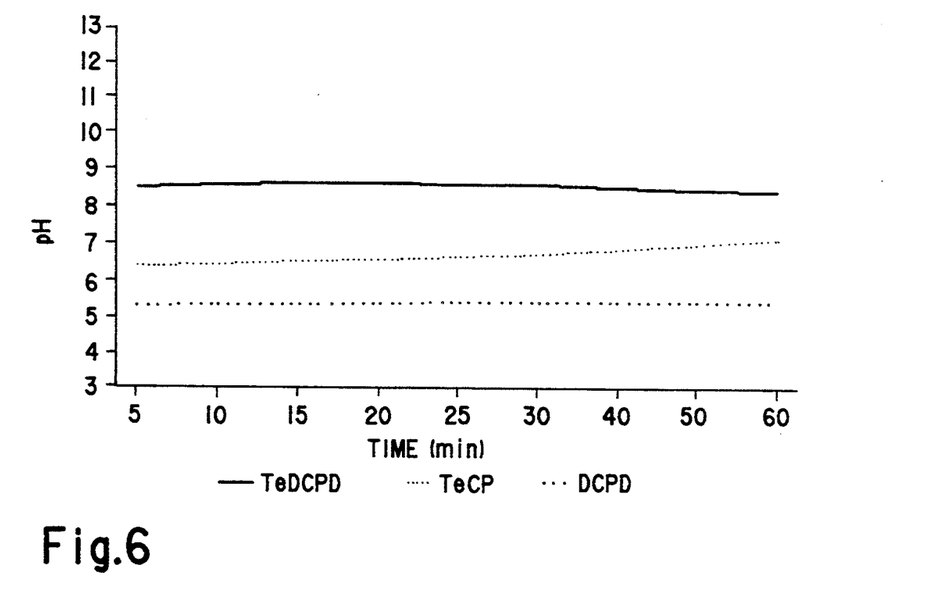
FIG. 6 shows changes in pH of the neighborhood of the pastes over time of the hardening material Example 32 and the materials using different powder components from the start of kneading.

As can be seen in FIGS. 5 and 6, the pH of the neighborhood of the pastes kneaded with the disodium hydrogen phosphate-citric acid type buffer solutions rose gradually from pH about 6.5 for the paste using the tetracalcium phosphate powder and lay constantly at pH near 5.6 for that using the calcium hydrogen phosphate powder. However, for the TeDCPD pastes (Examples 31 and 32), the pH values were not between the curves TeCP and DCPD from the start of kneading for the entire period measured and in contrast to these curves, showed less fluctuation, and lay constantly at a weakly basic (pH about 8.5).

In contrast, in the case of kneading with liquid components other than the disodium hydrogen phosphate-citric acid type buffer solutions, there were the following problems:

As can be seen in FIG. 7, the pH values of the neighborhood of the pastes kneaded with distilled water were stabilized at pH about 12.3 for the tetracalcium phosphate powder paste and at pH about 7.8 for the calcium hydrogen phosphate powder paste, and the TeDCPD paste (Reference Example 21) showed almost same behavior as the curve TeCP throughout i tom the start of kneading.

Figure 8:
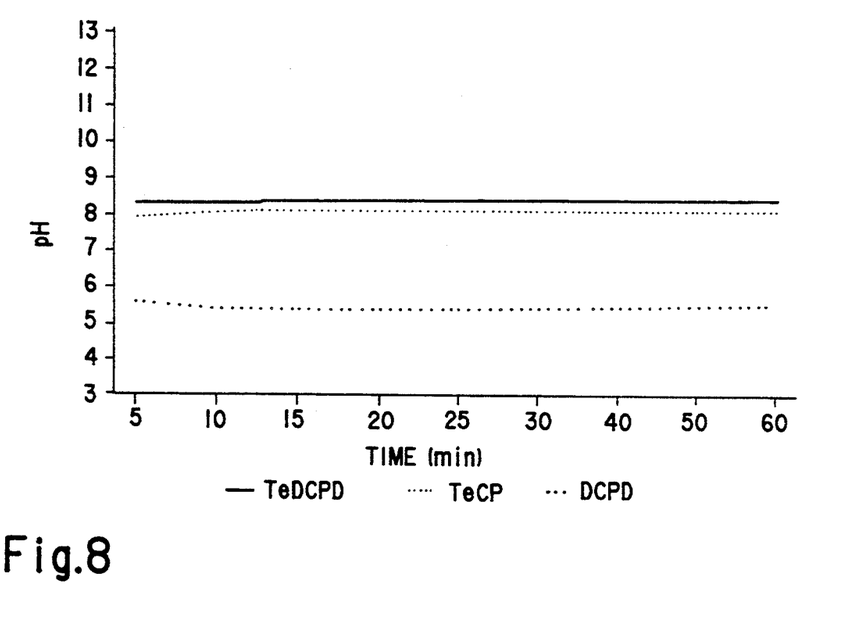
FIG. 8 shows changes in pH of the neighborhood of the pastes over time of the hardening material in Reference Example 23 and the materials using different powder components from the start of kneading.

As can be seen in FIG. 8, the. pH values of the neighborhood of the pastes kneaded with the 20 mM aqueous orthophosphoric acid solution were stabilized at pH about 8 for the tetracalcium phosphate power paste, slightly fluctuated around pH 5.5 for the calcium hydrogen phosphate powder paste, and lay constantly at pH about 8.3 throughout from the start of kneading for the TeDCPD paste (Reference Example 23).

Figure 9:
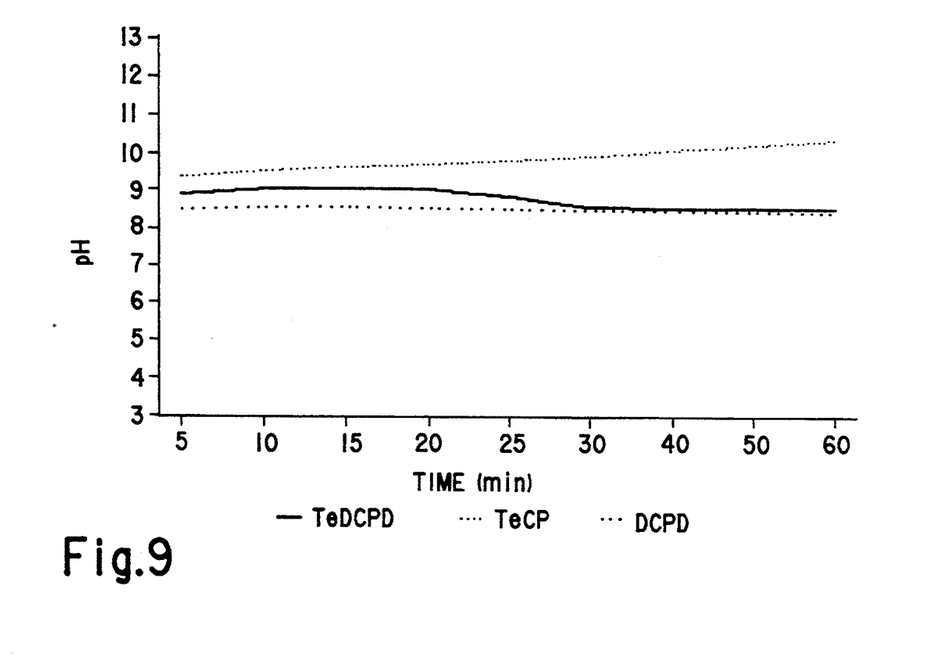
FIG. 9 shows changes in pH of the neighborhood of the pastes over time of the hardening material in Reference Example 24 and the materials using different powder components from the start of kneading.

As can be seen in FIG. 9, the pH values of the neighborhood of the pastes kneaded with the 0.2 M aqueous disodium hydrogen phosphate solution rose from about 9.4 for the tetracalcium phosphate paste, lay constantly at pH about 8.6 for the calcium hydrogen phosphate paste, was there between the curves TeCP and DCPD initially and showed the same behavior as the curve DCPD finally for the TeDCPD paste (Reference Example 24).

Figure 10:
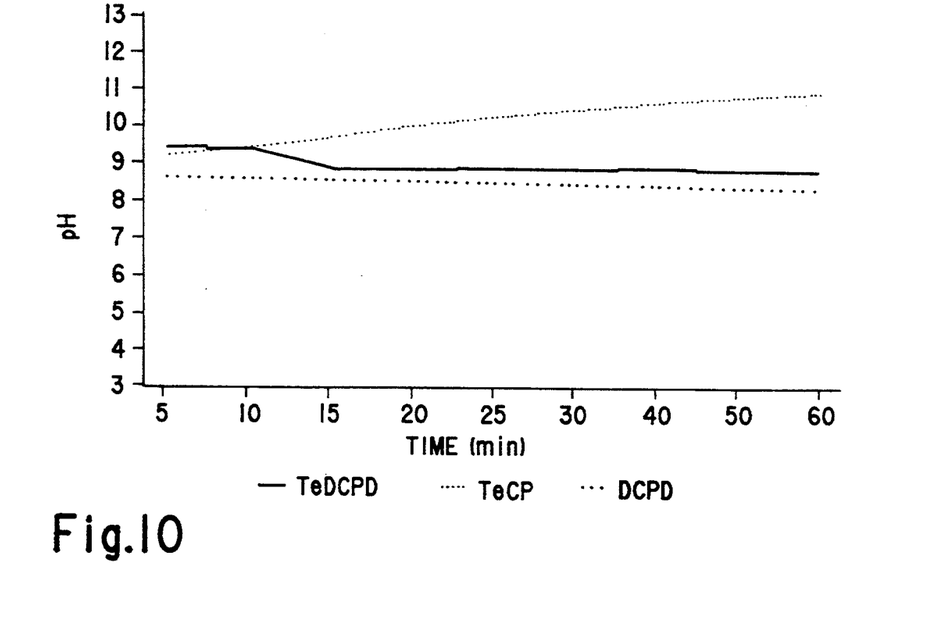
FIG. 10 shows changes in pH of the neighborhood of the pastes over time of the hardening material in Reference Example 25 and the materials using different powder components from the start of kneading.

As can be seen in FIG. 10, the pH values of the disodium hydrogen phosphate solution rose from pH about 9.2 for the tetracalcium phosphate paste, lay constantly at pH about 8.7 for the calcium hydrogen phosphate, and showed different behavior from the curves TeCP and DCPD for the TeDCPD paste (Reference Example 25). Thus, the pH values were once stabilized at pH about 9.5 initially, then lowered, and were stabilized at pH about 9 finally.

Figure 11:
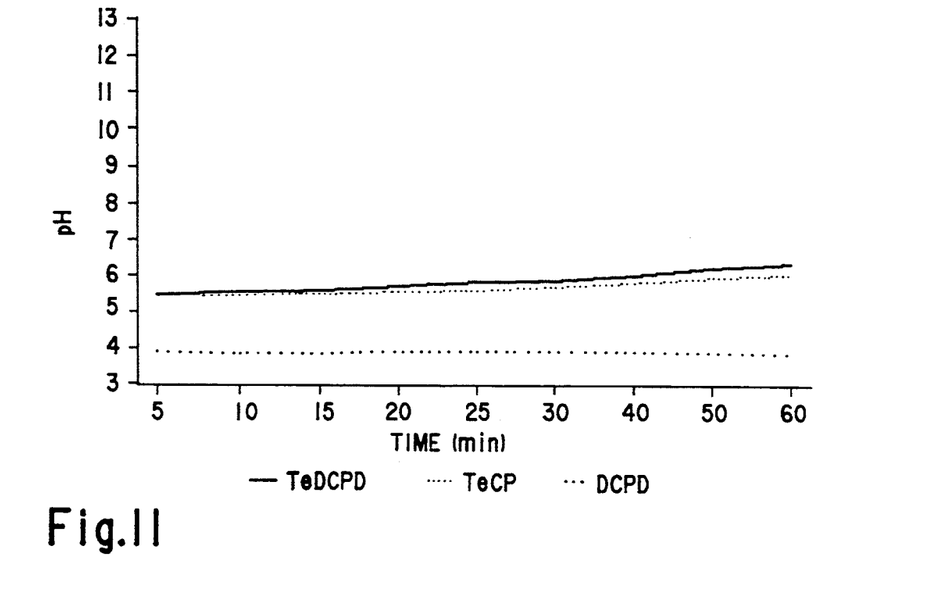
FIG. 11 shows changes in pH of the neighborhood of the pastes over time of the hardening material in Reference Example 26 and the materials using different powder components from the start of kneading.

As can be seen in FIG. 11, the pH values of the neighborhood of the pastes kneaded with the 0.1 M aqueous citric acid solution rose gradually from pH about 5.5 for the tetracalcium phosphate paste, slightly fluctuated at near pH 4 for the calcium hydrogen phosphate paste and showed almost same behavior as the curve TeCP throughout from the start of kneading for the TeDCPD paste (Reference Example 26).

Figure 12:
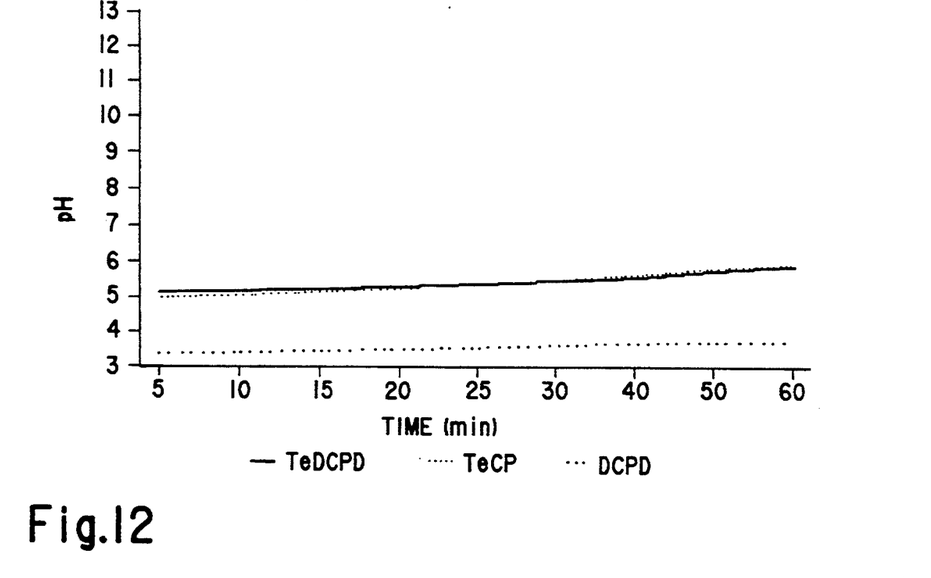
FIG. 12 shows changes in pH of the neighborhood of the pastes over time of the hardening material in Reference Example 27 and the materials using different powder components from the start of kneading.

As can be seen in FIG. 12, the pH values of the neighborhood of the pastes kneaded with the 0.2 M aqueous citric solution rose gradually from pH about 5 and 3.4 for the tetracalcium phosphate acid calcium hydrogen phosphate pastes, respectively, and showed the same behavior as the curve TeCP for the TeDCPD paste (Reference Example 27).

The reason why the fluctuations of the pH of the neighborhood of the TeDCPD pastes are different between FIGS. 4 and 7–12 is because of the difference of the powder to liquid ratio used.

From the above results, when the kneading solutions are weakly acidic solutions, it is expected that tetracalcium phosphate in TeDCPD first dissolves in the solutions. Considering that when tetracalcium phosphate and calcium hydrogen phosphate were kneaded with tile disodium hydrogen phosphate-citric acid type buffer solutions, respectively, the pH values of the neighborhood of these pastes were about 7 and 5.5, respectively, at 1 hour after the start of kneading, it is assumed that the dissolution of tetracalcium phosphate (formula 3) or the dissolution of tetracalcium phosphate and calcium hydrogen phosphate (formulae 1 and 3) was fast.

Since the dissolution shown in formulae 1 and 3 proceeds in an extremely short time because of the presence of the disodium hydrogen phosphate and citric acid, which are original solutes, and the elutes from tetracalcium phosphate and calcium hydrogen phosphate, equilibrium is reached immediately after kneading.

When the pH value of the solution is near 8.5 after equilibrium is reached, the reached shown in the formula 2 proceeds until all of the calcium hydrogen phosphate convert into hydroxyapatite while the pH is maintained at near 8.5. The $H_3PO_4$ formed by the reaction comes to solution-equilibrium with the disodium hydrogen phosphate and citric acid during kneading. If the pH is still maintained at near 8.5, the reaction of the formula 4 also proceeds and the tetracalcium phosphate converts into hydroxyapatite. The $Ca(OH)_2$ by product of this reaction comes to solution-equilibrium with $H_3PO_4$ produced from calcium hydrogen phosphate and disodium hydrogen phosphate and citric acid in kneading solutions, and the reaction shown as the formulae 7 and 8 proceeds:

$$2Ca^{2+} + HPO_4^{2-} + 2OH^- \rightarrow Ca_2(HPO_4)(OH)_2 \qquad (7)$$

$$4[Ca_2(HPO_4)(OH)_2] + 2Ca^{2+} + 2HPO_4^{2-} \rightarrow Ca_{10}(PO_4)_6(OH)_2 + 6H_2O \qquad (8)$$

The hardening material described in U.S. Pat. No. 4,518,430 is a material in which calcium hydrogen phosphate and tetracalcium phosphate cause hydration-reaction by kneading both the phosphates with, for example, a diluted orthophosphoric acid solution to convert into hydroxyapatite, resulting in coagulation-hardening. This hydration-reaction occurs at pH about 7.5 at which the solubility curves of the both phosphates cross. In the hydration-reaction of calcium phosphates, the pH of the neighborhood of the pastes largely fluctuates even when the condition such as mean particle size of powder, concentration of kneading solution, and powder to liquid ratio is slightly different. Because of this reason, it difficult to maintain the pH of the neighborhood of the pastes at pH near 7.5 upon hydration-reaction of calcium hydrogen phosphate and tetracalcium phosphate. Even if the pH were maintained at the pH, the above condition would extremely be limited. As can be seen in FIGS. 4 and 8 showing the results of Reference Example 23, the difference of powder to liquid ratio provided a large difference in the pH of the neighborhood of the pastes even when the phosphoric acid solution of the same concentration was used.

In contrast, for the disodium hydrogen phosphate-citric acid type buffer solutions, the pH of the neighborhood of the pastes is not affected at all by the difference in the powder to liquid ratio and in the concentration of the solutes in the buffer solutions and is stabilized similarly.

As shown in Table 7, TeDCPD hardened in 6 and 8 minutes when kneaded with the disodium hydrogen phosphate solutions and did not harden when kneaded with the aqueous citric acid solutions. From these results, it is clear that, when TeDCPD is kneaded with disodium hydrogen phosphate-citric acid type buffer solutions to result in hardening the necessary compound for hardening is the secondary phosphate ion. Therefore, the setting time can be controlled by regulating the pH and concentration of the solute in the kneading solution. This was also verified by the result that increase in concentration of secondary phosphate and organic acid ions caused faster setting time.

When kneading solution contains organic acid ions, a chelating reaction occurs between calcium and the ions to a small extent, and hence viscosity develops on kneading.

EXAMPLES 36-40

Hardening materials in the present invention are prepared using the combinations of the powder component obtained in the example 2 for preparation of powder component and the liquid components shown in Table 8.

REFERENCE EXAMPLES 28 AND 29

Hardening materials are prepared using the combinations of the powder component in the example 2 and the liquid components shown in Table 8.

The materials in Examples 36-40 and Reference Examples 28 and 29 were kneaded using the powder to liquid ratio (powder weight/liquid weight) shown in Table 8 to examine kneading-precessability, setting time, and pH of the neighborhood of the pastes (at 5 and 20 minutes after the start of kneading) by the above-described methods, and the adhesion to lentulo was also examined by the method described below. The results are shown in Table 8.

Adhesion to lentulo

The materials from which the pastes adhere uniformly to lentulo (a filling tool for dental root canal sealing materials) are judged as 'good adhesion'.

TABLE 8

|  | EXAMLE | | | | | REFERENCE EXAMPLE | |
|---|---|---|---|---|---|---|---|
|  | 36 | 37 | 38 | 39 | 40 | 28 | 29 |
| Liquid Component | Soln. A | Soln. B | Soln. C | Soln. D | Soln. E | Soln. F | Soln. G |
| Powder/Liquid Wt. Ratio | 1.2 | 1.2 | 1.2 | 1.2 | 1.2 | 1.2 | 1.2 1.6 |
| Kneading-Processability | excellent | excellent | excellent | excellent | excellent | poor | poor poor |
| Adhesion | good | good | good | good | good | n.a. | n.a. n.a. |
| Setting Time (min.) | 40 | 15 | 15 | 8 | 8 | n.h. | n.h. n.h. |
| pH of Neighbor-  After 5 min. | 8.56 | 8.57 | 8.33 | 8.34 | 8.47 | 13.15 | 10.30 12.30 |
| hood of Paste  After 20 min. | 8.70 | 8.67 | 8.47 | 8.11 | 8.16 | 13.34 | 11.00 12.51 |

Soln. A; buffer solution 1 in Table 5 containing 2.5 wt. % carboxymethyl cellulose sodium
Soln. B; buffer solution 2 in Table 5 containing 2.5 wt. % carboxymethyl cellulose sodium
Soln. C; buffer solution 2 in Table 5 containing 6.0 wt. % poly(sodium γ-glutamate
Soln. D; buffer solution 4 in Table 5 containing 2.5 wt. % carboxymethyl cellulose sodium
Soln. E; buffer solution 4 in Table 5 containing 6.0 wt. % poly(sodium γ-glutamate)
Soln. F; distilled water containing 2.5 wt. % carboxymethyl cellulose sodium
Soln. G; 20 mM H$_3$PO$_4$ solution containing 2.5 wt. % carboxymethyl cellulose sodium
n.a.; not adhered to lentulo
n.h.; not hardened Although, when TeDCPD was kneaded with the solutions containing secondary phosphate and organic acid ions, viscosity came slightly, the disodium hydrogen phosphate-citric acid type and disodium hydrogen phosphate-malic acid type buffer solutions containing carboxymethyl cellulose sodium or poly (sodium glutamate) were excellent as solutions providing cobwebbing property, as shown in Table 8. The addition of carboxymethyl cellulose sodium to distilled water or 20 mM orthophosphoric acid caused worse kneading-processability and disappearance of hardenability.

In general, it is known that viscosity is affected strongly by pH value in case of using thickeners such as carboxymethyl cellulose sodium, poly (sodium glutamate) to enhance the liquid viscosity. Since such thickeners are effective to increase viscosity in near neutral regions, they show no affect when used in highly basic pastes. In contrast, the addition of these thickeners to the secondary phosphate ion-organic acid ion type buffer solutions, which are the liquid components of the hardening materials wherein the pH of the neighborhood of their pastes stabilizes in the weakly basic region immediately after kneading, is useful for enhancing viscosity and, in addition, for providing pastes with the cobwebbing property.

What is claimed are:

1. A hardenable, biocompatible composition for repairing living tissue comprising
   a powder component containing Ca$_4$P$_2$O$_9$ and at least one of CaHPO$_4$ and CaHPO$_4$.2H$_2$O at a molar ratio of Ca:P of 1.16–.1.95; and
   a liquid component containing a secondary phosphate ion in a concentration of 1 mM to 2 M as a secondary phosphate and an organic acid ion in a concentration of 1 mM to 2 M as an organic acid or as a total of an organic acid and its salt, wherein a weight ratio of the powder component: the liquid component is 0.5–4.0.

2. A hardenable, biocompatible composition as defined in claim 1 having a pH range of about 8–9.

3. A hardenable, biocompatible composition as defined in claim 1, wherein the secondary phosphate ion source is a member of the group consisting of disodium hydrogen phosphate, dipotassium hydrogen phosphate, and diammonium hydrogen phosphate.

4. A hardenable, biocompatible composition as defined in claim 1, wherein the powder component has a mean particle size range of about 0.1–50 μm.

5. A hardenable, biocompatible composition as defined in claim 1, wherein the organic acid is a member of the group consisting of citric acid, malic acid, malonic acid, maleic acid, fumaric acid, fumaleic acid, lactic acid,, acetic acid, oxalacetic acid, isocitric acid, aconitric acid, succinic acid, acrylic acid homopolymer, acrylic acid-itaconic acid copolymer or salts thereof.

6. A hardenable, biocompatible composition as defined in claim 1, wherein the organic acid is a member of the group consisting of citric acid, and metabolism products of citric acid or salts thereof.

7. A hardenable, biocompatible composition as defined in claim 1, further comprising at least one thickener selected from the group consisting of carboxymethyl cellulose, sodium carboxymethyl cellulose, hydroxypropyl cellulose, polyvinyl alcohol, polyglutamic acid, polygultamic acid salt, polyaspartic acid, and polyaspartic acid salt, wherein the concentration of polyglutamic acid and polyglutamic acid salt is 0.5–15% by weight and the concentration of the other thickeners is 0.5–10% by weight.

8. A hardenable, biocompatible composition as defined in claim 1, further comprising at least one thickener selected from the group consisting of sodium carboxymethyl cellulose, hydroxypropyl cellulose, polyglutamic acid, and polyglutamic acid salt.

9. A hardenable, biocompatible composition as defined in claim 1, further comprising an X-ray contrast medium.

* * * * *